United States Patent

Gobbini et al.

[11] Patent Number: 5,955,632
[45] Date of Patent: Sep. 21, 1999

[54] SECO-D STEROIDS ACTIVE ON THE CARDIOVASCULAR SYSTEM, PROCESSES FOR THEIR PREPARATION AND PHARMACEUTICAL COMPOSITIONS CONTAINING THEM

[75] Inventors: Mauro Gobbini, Mercallo; Sergio De Munari, Milan; Giorgio Fedrizzi, Treviglio; Patrizia Ferrari, Varese; Piero Melloni, Bresso; Marco Santagostino, Magenta; Marco Torri, Rho, all of Italy

[73] Assignee: Sigma-Tau Industrie Farmaceutiche Riunite S.p.A., Rome, Italy

[21] Appl. No.: 08/891,033

[22] Filed: Jul. 10, 1997

[30] Foreign Application Priority Data

Aug. 19, 1996 [DE] Germany ............ 196 33 76

[51] Int. Cl.⁶ .............. C07D 295/04; C07D 211/06; A61K 31/495; C07C 291/00
[52] U.S. Cl. ............ 564/230; 564/253; 564/257; 564/3; 548/569; 546/263; 546/204; 514/248; 514/447; 514/634; 514/631; 514/640
[58] Field of Search .............. 564/253, 257, 564/230; 548/569; 546/203, 204; 514/248, 447, 634, 631, 640

[56] References Cited

U.S. PATENT DOCUMENTS 5,731,345  3/1998  Gobbini et al. .............. 514/461

*Primary Examiner*—José G. Dees
*Assistant Examiner*—Sabiha N. Qazi
*Attorney, Agent, or Firm*—Oblon, Spivak, McClelland, Maier & Neustadt, P.C.

[57] ABSTRACT

New seco-D steroid derivatives, processes for their preparation and pharmaceutical compositions are provided, which are active on the cardiovascular system. The seco-D steroid derivatives have the following general formula (I):

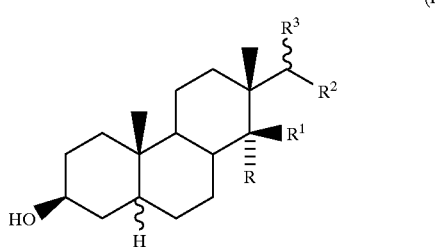

6 Claims, No Drawings

SECO-D STEROIDS ACTIVE ON THE CARDIOVASCULAR SYSTEM, PROCESSES FOR THEIR PREPARATION AND PHARMACEUTICAL COMPOSITIONS CONTAINING THEM

The present invention relates to new seco-D steroid derivatives, active on the cardiovascular system, to a process for their preparation and to pharmaceutical compositions containing them. The compounds described in the present invention are useful in the treatment of cardiovascular diseases such as heart failure and hypertension.

The compounds claimed show a high binding affinity for the digitalis receptor site on the $Na^+,K^+$-ATPase and are active on the cardiovascular system, in spite of the lack of some structural requirements considered of fundamental importance for the natural digitalis compounds such as digoxin, ouabain and digitoxigenin.

These requirements are: the cyclopentanperhydrophenanthrene skeleton; the cis junction between A/B and C/D rings and the presence of a 17β-unsaturated lactone (Repke K. R. H., Schönfeld W. (1984); $Na^+/K^+$-ATPase as the digitalis receptor; *Trends Pharmacol. Sci.* 5: 393–397; Thomas R., Gray P., Andrews J. (1990); Digitalis: its mode of action, receptor, and structure-activity relationships; *Adv. Drug Res.* 19: 312–562).

The invention relates to compounds of general formula (I)

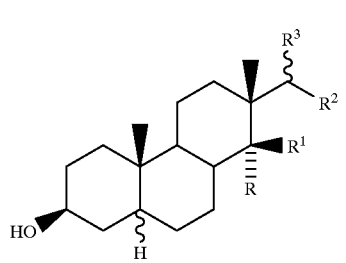

wherein:
- the symbol ⌇ means that the hydrogen in position 5 and the substituent $R^3$ in positon 17 can have an α or β configuration.
- R and $R^1$ are respectively hydrogen and hydroxy, or R and $R^1$ taken together form a keto group;
- $R^2$ is methyl, ethyl or propyl;
- $R^3$ is $(CH_2)_{0-1}$—CH=N ⌇ $R^4$ or $CH_2$—CH=CH—CH=N ⌇ $R^4$;
  wherein
  the symbol ⌇ means that both the Z isomer and the E isomer are considered;
  $R^4$ is $NHC(=NH)NR^5R^6$ or $OR^7$;
    wherein
    $R^5$, $R^6$ are independently hydrogen, C1–C4 alkyl or $R^5$ and $R^6$ taken together form, with the nitrogen they are linked to, a saturated five o six membered monoheterocyclic ring;
    $R^7$ is hydrogen, C1–C6 alkyl, unsubstituted or substituted by $NR^8R^9$;
      wherein
      $R^8$, $R^9$ are independently hydrogen or C1–C4 alkyl Also the pharmaceutically acceptable salts of compounds of general formula (I) are included in the scope of the invention.

Pharmaceutically acceptable salts of (I) are salts which retain the biologically activity of the base and are derived from such known pharmacologically acceptable acids such as hydrochloric, hydrobromic, sulphuric, phosphoric, fumaric, succinic, oxalic, malic, tartaric, maleic, citric, methanesulphonic or benzoic acids.

The alkyl groups may be branched or straight chain groups.

The C1–C6 alkyl group is preferably a C1–C4 alkyl group, e.g. methyl, ethyl, propyl, isopropyl, butyl, sec-butyl, tert-butyl.

The C1–C4 alkyl group is preferably methyl, ethyl, propyl, isopropyl, butyl, sec-butyl, tert-butyl.

The $NR^5R^6$ group is preferably amino, methylamino, dimethylamino, diethylamino, 1-pyrrolidinyl, piperidino.

The $NHC(=NH)NR^5R^6$ group is preferably a guanidino group.

The $OR^7$ group is preferably 2-aminoethoxy, 2-dimethylaminoethoxy.

Preferred examples of specific compounds according to the present invention are:

E-17β-2-[(2-Aminoethoxy)iminomethyl]-5β-14,15-seco-3β-hydroxy-androstan-14-one

E-17α-2-[(2-Aminoethoxy)iminomethyl]-5β- 14,15-seco-3β-hydroxy-androstan-14-one

E-17β-Methyl-15-[(2-aminoethoxy)imino]-5β- 14,15-seco-3β-hydroxy-androstan-14-one E-17β-Methyl-15-[(2-dimethylaminoethoxy)imino]-5β-14,15-seco-3β-hydroxy-androstan-14-one E-17β-2-[(2-Dimethylaminoethoxy)iminomethyl]-5β-14,15-seco-3β-hydroxy-androstan-14-one E-17α-2-[(2-Dimethylaminoethoxy)iminomethyl]-5β-14,15-seco-3β-hydroxy-androstan-14-one E-17β-2-[(2-Aminoethoxy)iminoethyl]-5β-14,15-seco-3β-hydroxy-androstan-14-one E-17α-2-[(2-Aminoethoxy)iminoethyl]-5β-14,15-seco-3β-hydroxy-androstan-14-one E-17β-2-[(2-Dimethylaminoethoxy)iminoethyl]-5β-14,15-seco-3β-hydroxy-androstan-14-one E-17α-2-[(2-Dimethylaminoethoxy)iminoethyl]-5β-14,15-seco-3β-hydroxy-androstan-14-one E-17α-2-[(2-Aminoethoxy)iminoethyl]-5β-14,15-seco-3β,14β-dihydroxy-androstane E-17α-2-[(2-Dimethylaminoethoxy)iminoethyl]-5β-14,15-seco-3β,14β-dihydroxy-androstane E-17α-(2-Guanidinoiminoethyl)-5β-14,15-seco-3β-hydroxy-androstan-14-one E-17β-Propyl-15-[(2-aminoethoxy)imino]-5β-14,15-seco-3β-hydroxy-androstan-1 4-one E-17β-Propyl-15-[(2-dimethylaminoethoxy)imino]-5β-14,15-seco-3β-hydroxy-androstan-14-one E,E-17α-4-[(2-Dimethylaminoethoxyimino)-2-butenyl]-5-14,15-seco-3β-hydroxy-androstan-14-one E-17α-2-[(2-Aminoethoxy)iminoethyl]-14,15-seco-3β-hydroxy-androstan-14one E-17α-2-[(2-Dimethylaminoethoxy)iminoethyl]-14,15-seco-3β-hydroxy-androstan-14-one E-17α-(2-Guanidinoiminoethyl)-14,15-seco-3β-hydroxy-androstan-14-one Preferred compounds are also the corresponding Z isomer derivatives.

The invention furthermore provides a process for the preparation of compounds of general formula (I) wherein $R^3$ is $(CH_2)_{0-1}$—CH=N~ $R^4$ which comprises a condensation reaction of compounds of formula (II)

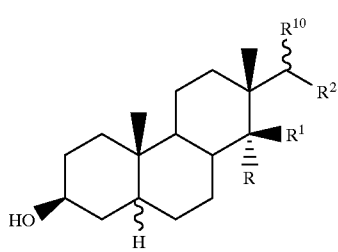

II in which: the symbol ~ and the substituent $R^2$ is as above defined, R and $R^1$ form a keto group and $R^{10}$ is CHO or $CH_2$—CHO with a compound of general formula (III) or (IV)

$H_2NNHC(=NH)NR^5R^6$     III $H_2NOR^7$     IV where $R^5$, $R^6$ and $R^7$ are as above defined, to give compounds of general formula I where $R^3$ is $(CH_2)_{0-1}$—CH=N~ $R^4$.

Compounds (III) and (IV) can be used as the free base or in the form of a salt with an acid such as, e.g., hydrochloric, carbonic, oxalic, hydriodic or sulfuric acid. The reaction can be carried out in a solvent, such as ethanol, methanol, acetonitrile, dioxane, tetrahydrofuran, water or a mixture of said solvents, at a temperature between 0° C. and the boiling point of the above mentioned solvents or of their mixtures. To the reaction mixtures, additional salts, such as, e.g., $NaH_2PO_4$, $Na_2HPO_4$, NaOAc, can be added as well as acids such as, e.g., hydrochloric, sulfuric, acetic, phosphoric acid, and bases such as, e.g., sodium or potassium hydroxide, to maintain the desired pH.

Compounds of general formula (1) wherein $R^3$ is $CH_2$—CH=CH—CH=N~ $R^4$, are prepared by a condensation reaction of compounds of formula (II) wherein $R^{10}$ is $CH_2$—CHO with a compound of general formula (V) and (VI)

$(EtO)_2POCH_2$—CH=NH—NHC(=NH)$NR^5R^6$     V $(EtO)_2POCH_2$—CH=$NOR^7$     VI where $R^5$, $R^6$ and $R^7$ are as above defined.

The reaction can be carried out in a solvent such as tetrahydrofuran or toluene or a mixture of said solvents, at a temperature between -78° C. and room temperature, in the presence of a strong base such as sodium hydride, potassium hydride, butyllithium.

Compounds of general formula (I) prepared as described above wherein $R^3$ is as above defined, R and $R^1$ taken together form a keto group may be converted into another compound of general formula (I) wherein $R^3$ is as above defined, R and $R^1$ are respectively hydrogen and hydroxy by reduction of the keto group with complex hydrides, e.g. $NaBH_4$, tri-tert-butoxyaluminum hydride, $NaCNBH_3$. The reaction can be carried out in a solvent, such as ethanol, methanol, dioxane, tetrahydrofuran or a mixture of said solvents, possibly in the presence of water, at a temperature between -78° C. and the room temperature. To the reaction mixtures, additional salts, such as, e.g., $NaH_2PO_4$, $Na_2HPO_4$, NaOAc, can be added as well as acids such as, e.g., hydrochloric, sulfuric, acetic, phosphoric acid, and bases such as, e.g., sodium or potassium hydroxide, to maintain the desired pH. The reduction of the keto group leads to a mixtures of β/α isomers, the specific ratio depending on the structure of the starting compound and of the reaction conditions; the desired β isomer could be isolated both by cristallization in solvents such as ethanol, methanol, ethyl acetate, hexane, cyclohexane, diethyl ether or mixtures of said solvents, or by chromatography purification on silica gel using solvents such as ethyl acetate, hexane, cyclohexane, diethyl ether or a mixture of said solvents as the mobile phase.

Compounds of general formula (II) wherein the symbol ~ and the substituent $R^2$ are as above defined, R and $R^1$ form a keto group and $R^{10}$ is $CH_2$—CHO are prepared by ozonolysis of compounds of general formula (VII)

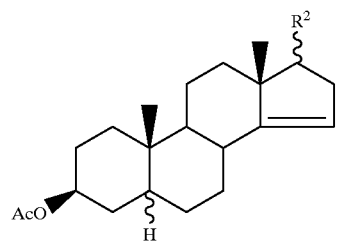

VII

The reaction can be carried out in a solvent, such as ethanol, methanol, dioxane, tetrahydrofuran, chloroform, methylene dichloride or mixtures of said solvents, at a temperature between -78° C. and room temperature. The ozonide obtained can be reduced to the desired product by treating the reaction mixture with a reducing agent such as: zinc in the presence of acetic acid, dimethyl sulfide, sodium sulfite, thiourea, methyl phosphite or ethyl phosphate, at a temperature between -30° C. and the room temperature. The ozonide can also be isolated from the reaction mixture and then reduced by dissolving it in a solvent such as ethanol, methanol, dioxane, tetrahydrofuran, chloroform, methylene dichloride or mixtures of said solvents and reacting with a reducing agent as described above. The protective group present in position 3 is then removed by known methods.

Compounds of general formula (II) wherein the symbol ~ and the substituent $R^2$ are as above defined, R and $R^1$ form a keto group and $R^{10}$ is CHO are prepared from compounds of general formula (II) wherein $R^{10}$ is $CH_2$—CHO by reaction with acetic anhydride in the presence of triethylamine in a solvent such as tetrahydrofuran, chloroform, methylene dichloride or mixtures of said solvents at a temperature between -30° C. and the boiling point of the solvent or mixtures of solvents, to give the enolacetate of the aldehyde that was in turn treated with ozone as described above.

Compounds of general formula (VII) wherein the symbol ~ is as above defined and the substituent $R^2$ is methyl, are prepared from compounds of general formula (VIII) wherein the substituent $R^{11}$ is H or represents a protective group, by reaction with $SOCl_2$ in pyridine or $POCl_3$ in pyridine both at a temperature between 0° C. and the room temperature or by reaction with diluted mineral acids such as hydrochloric or sulfuric acid in methanol/water or ethanol/water at room temperature, or p-toluensulfonic acid in toluene at a temperature between the room temperature and the boiling point of the solvent.

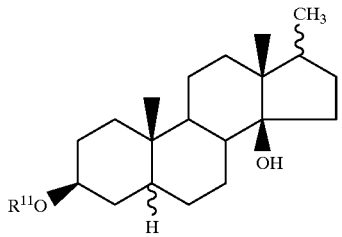

VIII

Compounds of general formula (VIII) wherein the symbol ⌇ and substituent $R^{11}$ are as above defined, are prepared by deoxygenation of the oxo function of compounds of general formula (IX).

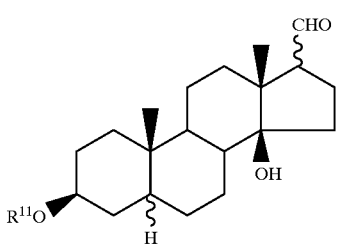

IX

Where $R^{11}$ is as above defined.

The reaction can be carried out by treating a compound of general formula (IX) dissolved in a polar protic solvent such as methanol, ethanol, acetic acid or a mixture of said solvents, with p-toluensulfonic hydrazide at a temperature between the room temperature and the boiling point of the above mentioned solvents or their mixtures. The p-toluensulfonic hydrazone obtained was in turn reduced by adding to the reaction mixture a reducing agent such as $NaBH_4$ or $NaCNBH_3$ possibly in the presence of a catalytic amount of zinc iodide or zinc chloride, at a temperature between room temperature and the boiling point of the above mentioned solvents or their mixtures. Alternatively the p-toluensulfonic hydrazone obtained was isolated from the reaction mixture and reduced by dissolving it in a polar protic solvent such as methanol, ethanol, acetic acid or a mixture of said solvents, and treated with a reducing agent such as $NaBH_4$ or $NaCNBH_3$ possibly in the presence of a catalytic amount of zinc iodide or zinc chloride, at a temperature between the room temperature and the boiling point of the above mentioned solvents or of their mixtures.

Compounds of general formula (IX) wherein $R^{11}$ is H or Ac are known compounds: 5β,17β (Boutagy J. and Thomas R. *Aust. J. Chem.,* 1971, 24, 2723); 5β,17α (Boutagy J. and Thomas R. *Aust. J. Pharm. Sc.,* 1973, NS2, 9). The 5α,17β derivative is prepared from the commercially available uzarigenin following the procedure described by Boutagy for the analogous transformation from digitoxigenin (Boutagy J. and Thomas R. *Aust. J. Chem.,* 1971, 24, 2723); 5α,17α derivative is prepared from the corresponding 5α,17β epimeric compound by isomerization in alkaline conditions.

Compounds of general formula (VII) wherein the symbol ⌇ is as above defined and the substituent $R^2$ is ethyl, are prepared by deoxygenation of the oxo function of compounds of general formula (X).

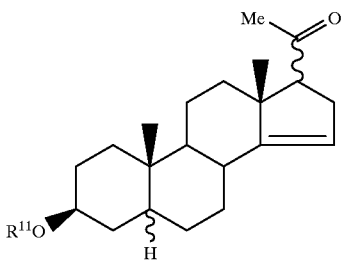

X wherein $R^{11}$ is as above defined, as described above for compounds of general formula (IX).

Compounds of general formula (X), wherein $R^{11}$ is H or Ac are known compounds: 5β,17β (Donovan S. F. et al. Tetrahedron Lett. 1979, 35, 3287); 5α,17β (Nambara T. et al. Chem. Pharm. Bull. 1970, 18, 453); 5α,17α (Weiss E. et al. Helv. Chim. Acta 1969, 52, 2583). The unknown compound 5β,17α is prepared from the corresponding 5β,17β epimeric compound by isomerization in alkaline conditions.

Compounds of general formula (VII) wherein the symbol ⌇ is as above defined and the substituent $R^2$ is propyl, are prepared from compounds of general formula (IX) wherein $R^{11}$ is t-butyldimethylsilyl, by reaction with EtMgBr in solvents such as ether or THF or a mixture of said solvents, at a temperature between the room temperature and the boiling point of the above mentioned solvents or of their mixtures. The secondary alcohols obtained was in turn deoxygenated using the Barton's procedure (Barton D. H. R. et al. *J. Chem. Soc. Perkin I,* 1975, 1574) to give the desired compounds.

Compounds of general formula (III), (IV), (V) and (VI) are known compounds, generally commercially available or preparable from known compounds by known methods.

All the chemical reations described above are examples of general procedures of the organic chemistry (for example: J. March "Advanced Organic Chemistry", J. Wiley & Sons, 1985; D. Barton and W. D. Ollis "Comprehensive Organic Chemistry", Pergamon Press, 1979).

Compounds of general formula (I) prepared according to the invention and their pharmaceutically acceptable salts are useful agents for the treatment of cardiovascular disorders such as heart failure and hypertension.

Compounds of general formula (I) prepared according to the invention and their pharmaceutically acceptable salts have a better terapeutic index compared to known positive inotropic agents such as digoxin and digitoxin. Said compounds (I) show good affinity for the receptor site of the $Na^+,K^+$-ATPase.

To test the affinity for the receptor site of the $Na^+,K^+$-ATPase and the agonist or antagonist activity on the enzyme, the following tests were used:

a) displacement of the specific $^3H$-ouabain binding from the $Na^+,K^+$-ATPase receptor purified according to Jorghensen (Jorghensen P., BBA, 1974, 356, 36) and Erdmann (Erdmann E. et al., *Arzneim. Forsh,* 1984, 34, 1314);

b) inhibition of the activity of the purified $Na^+,K^+$-ATPase measured as % of hydrolysis of $^{32}P$-ATP in presence and in absence of the tested compound (Doucet A. et al., *Am. J. Physiol.,* 1986, 251, F851).

To test the antihypertensive activity the following test was used:

systolic blood pressure (SBP) and heart rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5% (w/v), was orally given daily for at least 5 weeks to the treated groups. The control group received only Methocel. SBP and HR were measured weekly 6 and 24 hrs after treatment. After 5 weeks of treatment, when hypertension was fully developed in the control group (9 weeks of age), washout was started for at least one week, to verify whether the treatment mantained blood pressure low or reestablished the basal values.

The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., *Japan J. Pharmacol.*, 1979, 29,171; Takeda K. et al. *Japan J. Pharmacol.*, 1982, 32, 283; Richer C. et al. *Eur. J. Pharmacol*, 1978, 47,393).

The inotropic activity was measured in electrically paced guinea pig left atrium according to Bova (Bova S. et al., *Hypertension*, 1991, 17, 944).

The pharmacological profile of some compounds of general formula (I) on the above mentioned tests are shown in the following tables:

BINDING AFFINITY AND INHIBITORY ACTIVITY ON $Na^+,K^+$-ATPase

| Compound | Binding $^3$H-Ouab. Displacement -log IC50 | Inhibitory Activity -log IC50 |
| --- | --- | --- |
| Comp. I-ae | 7.0 | 6.0 |
| Comp. I-ag | 6.9 | 5.9 |
| Comp. I-ai | 5.4 | 4.0 |
| Comp. I-ak | 6.3 | 5.1 |
| Comp. I-ao | 7.4 | 6.7 |
| Comp. I-aq | 6.1 | 4.9 |
| Comp. I-as | 7.0 | 5.9 |
| Comp. I-ay | 6.4 | 5.5 |
| Comp. I-be | 6.5 | 5.2 |
| Comp. I-bg | 6.8 | 6.0 |
| Comp. I-bi | 5.7 | 5.0 |

EFFECT OF 5 WEEK-TREATMENT IN SPONTANEOUS HYPERTENSIVE RATS (MHS) ON THE DEVELOPMENT OF HYPERTENSION

| Compound | RATS | DOSE* mg/Kg/os | SBP mm Hg | HR beats/min. |
| --- | --- | --- | --- | --- |
| Controls | 7 | Methocel | 172 +/- 3.5 | 380 +/- 9.0 |
| Comp. I-ae | 7 | 1 | 149 +/- 3.7 | 370 +/- 11.2 |
| Comp. I-ag | 7 | 1 | 154 +/- 4.8 | 390 +/- 5.9 |
| Comp. I-ak | 7 | 1 | 153 +/- 6.3 | 380 +/- 10.0 |
| Comp. I-be | 7 | 1 | 150 +/- 5.1 | 384 +/- 7.9 |
| Comp. I-bg | 7 | 1 | 151 +/- 5.2 | 388 +/- 9.0 |

*in Methocel 0.5% w/v

INOTROPIC ACTIVITY ON GUINEA PIG LEFT ATRIUM

| Compound | Inotropic Effect % over basal | $IC_{50}$ [μM] |
| --- | --- | --- |
| Comp. I-ao | 109 | 2.2 |
| Comp. I-as | 90 | 1.5 |

The following examples illustrate the invention without limiting it.

EXAMPLE 1

E-17β-2-[(2-Aminoethoxy)iminomethyl]-5β-14,15-seco-3β-hydroxy-androstan-14-one oxalate (I-aa)
and Z-17β-2-[(2-Aminoethoxy)iminomethyl]-5β-14,15-seco-3β-hydroxy-androstan-14-one oxalate (I-ab)

To a solution of 5.0 g of 3β-acetoxy-14-oxo-17β-formyl-14,15-seco-5β-androstane (II-e, Prep. 10) and anhydrous sodium acetate (6.0 g) in dioxane (27 mL) and water (13 mL), 2-aminoethoxyamine dihydrochloride (2.7 g) was added and the reaction mixture was stirred at room temperature for 2.5 hr. The organic solvent was evaporated under reduced pressure, the acqueos suspension was extracted with EtOAc and the organic layer was dried over anhydrous sodium sulfate and evaporated to dryness. The crude residue was dissolved in MeOH (65 mL) and 28 mL of a IM solution of NaOH were added; the reaction mixture was stirred at room temperature for some hours and the organic solvent was evaporated under reduced pressure. The aqueous suspension was extracted with EtOAc and the organic layer was dried over anhydrous sodium sulfate and evaporated to dryness. The pure Z and E compounds obtained by flash-chromatography ($CHCl_3$/MeOH/NH4OH 98.5/2.5/0.25) were reacted with the stoichiometric equivalent of oxalic acid in diethyl ether to give 2.5 g of the E isomer (I-aa) and 0.8 g of the Z isomer (I-ab) as white solids.

E isomer (I-aa) $^1$H-NMR (300 MHz, $CD_3OD$, ppm from TMS): 0.89 (3H, t); 1.03 (3H, s); 1.18 (3H, s); 2.64 (1H, m); 3.02 (2H, m); 4.01 (1H, bs); 4.36 (2H, m); 7.52 (1H, d).

Z isomer (I-ab) $^1$H-NMR (300 MHz. $CD_3OD$, ppm from TMS): 0.91 (3H, t); 1.05 (3H, s); 1.21 (3H, s); 2.63 (1H, m); 3.03 (2H, m); 4.03 (1H, bs); 4.41 (2H, m); 6.84 (1H, d).

EXAMPLE 2

E-17α-2-[(2-Aminoethoxy)iminomethyl]-5β-14,15-seco-3β-hydroxy-androstan-14-one oxalate (I-ac)
and Z-17α-2-[(2-Aminoethoxy)iminomethyl]-5β-14,15-seco-3β-hydroxy-androstan-14-one oxalate (I-ad)

3β-Acetoxy-14-oxo-17α-formyl-14,15-seco-5β-androstane (II-c, Prep. 8) (3.2 g) was reacted with 2-aminoethoxyamine (33 mL of 1.4 M solution in THF) as described in Ex. 1; the pure Z and E compounds obtained by flash-chromatography were reacted with the stoichiometric equivalent of oxalic acid in diethyl ether to give 0.8 g of the E isomer (I-ac) and 0.6 g of the Z isomer (I-ad) as white solids.

E isomer (I-ac) $^1$H-NMR (300 MHz, $CD_3OD$, ppm from TMS): 0.81 (3H, t); 0.95 (3H, s); 1.07 (3H, s); 3.25 (2H, m); 3.80 (1H, bs); 4.27 (2H, m); 7.51 (1H, d).

Z isomer (I-ad) $^1$H-NMR (300 MHz, $CD_3OD$, ppm from TMS): 0.78 (3H, t); 0.95 (3H, s); 1.07 (3H, s); 3.25 (2H, m); 3.80 (1H, bs); 4.27 (2H, m); 6.90 (1H, d).

EXAMPLE 3

E-17β-Methyl-15-[(2-aminoethoxy)imino]-5β-14, 15-seco-3β-hydroxy-androstan-14-one oxalate (I-ae) and Z-17β-Methyl-15-[(2-aminoethoxy)imino]-5β-14,15-seco-3β-hydroxy-androstan-14-one oxalate (I-af)

3β-Acetoxy-14,15-dioxo-17β-methyl-14,15-seco-5β-androstane (II-a, Prep. 6) (3.0 g) was reacted with 2-aminoethoxyamine dihydrochloride (1.3 g) as described in Ex. 1; the pure Z and E compounds obtained by flash-chromatography were reacted with the stoichiometric equivalent of oxalic acid in diethyl ether to give 1.6 g of the E isomer (I-ae) and 0.2 g of the Z isomer (I-af) as white solids.

E isomer (I-ae) $^1$H-NMR (300 MHz, CD$_3$OD, ppm from TMS): 0.83 (3H, d); 1.07 (3H, s); 1.16 (3H, s); 3.21 (2H, bt); 4.02 (1H, bs); 4.20 (2H, bt); 7.53 (1H, dd).

Z isomer (I-af) $^1$H-NMR (300 MHz, CD$_3$OD, ppm from TMS): 0.85 (3H, d); 1.07 (3H, s); 1.16 (3H, s); 3.25 (2H, bt); 4.02 (1H, bs); 4.26 (2H, bt); 6.85 (1H, dd).

EXAMPLE 4

E-17β-Methyl-15-[(2-dimethylaminoethoxy)imino]-5β-14,15-seco-3β-hydroxy-androstan-14-one oxalate (I-ag) and Z-17β-Methyl-15-[(2-dimethylaminoethoxy)imino]-5β-14,15-seco-3β-hydroxy-androstan-14-one oxalate (I-ah)

3β-Acetoxy-14,15-dioxo-17β-methyl-14,15-seco-5β-androstane (II-a Prep. 6) (7.8 g) was reacted with 2-dimethylaminoethoxyamine dihydrochloride (5.0 g) as described in Ex. 1; the pure Z and E compounds obtained by flash-chromatography were reacted with the stoichiometric equivalent of oxalic acid in diethyl ether to give 1.5 g of the E isomer (I-ag) and 0.5 g of the Z isomer (I-ah) as white solids.

E isomer (I-ag) $^1$H-NMR (300 MHz, CD$_3$OD, ppm from TMS): 0.84 (3H, d); 1.06 (3H, s); 1.16 (3H, s); 2.95 (6H, s); 3.47 (2H, m); 4.03 (1H, bs); 4.32 (2H, m); 7.53 (1H, dd).

Z isomer (I-ah) $^1$H-NMR (300 MHz, CD$_3$OD, ppm from TMS): 0.86 (3H, d); 1.06 (3H, s); 1.16 (3H, s); 2.95 (6H, s); 3.47 (2H, m); 4.03 (1H, bs); 4.37 (2H, m); 6.88 (1H, bt).

EXAMPLE 5

E-17β-2-[(2-Dimethylaminoethoxy)iminomethyl]-5β-14,15-seco-3β-hydroxy-androstan-14-one oxalate (I-ai) and Z-17β-2-[(2-Dimethylaminoethoxy)iminomethyl]-5β-14,15-seco-3β-hydroxy-androstan-14-one oxala-te (I-aj)

3β-Acetoxy-14-oxo-17p-formyl-14,15-seco-5β-androstane (II-e, Prep. 10) (4.0 g) was reacted with 2-dimethylaminoethoxyamine (4.1 mL of 1.4 M solution in THF) as described in Ex. 1; the pure Z and E compounds obtained by flash-chromatography were reacted with the stoichiometric equivalent of oxalic acid in diethyl ether to give 1.8 g of the E isomer (I-ai) and 1.0 g of the Z isomer (I-aj) as white solids.

E isomer (I-ai) $^1$H-NMR (300 MHz, CD$_3$OD, ppm from TMS): 0.89 (3H, t); 1.03 (3H, s); 1.18 (3H, s); 2.64 (1H, m); 2.3 (6H, s); 3.46 (2H, m); 4.01 (1H, bs); 4.36 (2H, m); 7.52 (1H, d).

Z isomer (I-aj) $^1$H-NMR (300 MHz, CD$_3$OD, ppm from TMS): 0.91 (3H, t); 1.05 (3H, s); 1.21 (3H, s); 2.63 (1H, m); 3.01 (6H, s); 3.48 (2H, m); 4.01 (1H, bs); 4.41 (2H, m); 6.84 (1H, d).

EXAMPLE 6

E-17β-2-[(2-Dimethylaminoethoxy)iminomethyl]-5β-14,15-seco-3β-hydroxy-androstan-14-one oxalate (I-ak) and Z-17β-2-[(2-Dimethylaminoethoxy)iminomethyl]-5β-14,15-seco-3β-hydroxy-androstan-14-one oxalate (I-al)

3β-Acetoxy-14-oxo-17α-formyl-14,15-seco-5β-androstane (II-c, Prep. 8) (2.9 g) was reacted with 2-dimethylaminoethoxyamine (30 mL of 1.4 M solution in THF) as described in Ex. 1; the pure Z and E compounds obtained by flash-chromatography were reacted with the stoichiometric equivalent of oxalic acid in diethyl ether to give 0.4 g of the E isomer (I-ak) and 0.3 g of the Z isomer (I-al) as white solids.

E isomer (I-ak) $^1$H-NMR (300 MHz, CD$_3$OD, ppm from TMS): 0.80 (3H, t); 0.93 (3H, s); 1.07 (3H, s); 2.81 (6H, s); 3.32 (2H, m); 3.87 (1H, bs); 4.28 (2H, m); 7.53 (1H, d).

Z isomer (I-al) $^1$H-NMR (300 MHz, CD$_3$OD, ppm from TMS): 0.76 (3H, t); 0.93 (3H, s); 1.07 (3H, s); 2.81 (6H, s); 3.32 (2H, m); 3.87 (1H, bs); 4.28 (2H, m); 6.69 (11H, d).

EXAMPLE 7

E-17β-2-[(2-Aminoethoxy)iminomethyl]-5β-14,15-seco-3β-hydroxy-androstan-14-one oxalate (I-am) and Z-17β-2-[(2-Aminoethoxy)iminomethyl]-5β-14,15-seco-3β-hydroxy-androstan-14-one oxalate (I-an)

3β-Acetoxy- 14,15-dioxo- 17α-ethyl-14,15-seco-5β-androstane (II-d, Prep. 9) (2.5 g) was reacted with 2-aminoethoxyamine dihydrochloride (1.0 g) as described in Ex. 1; the pure Z and E compounds obtained by flash-chromatography were reacted with the stoichiometric equivalent of oxalic acid in diethyl ether to give 1.2 g of the E isomer (I-am) and 0.4 g of the Z isomer (I-an) as white solids.

E isomer (I-am) $^1$H-NMR (300 MHz, CD$_3$OD, ppm from TMS): 0.92 (3H, t); 1.02 (3H, s); 1.14 (3H, s); 2.64 (1H, m); 3.03 (2H, m); 4.02 (1H, bs); 4.32 (2H, m); 7.63 (1H, bt).

Z isomer (I-an) $^1$H-NMR (300 MHz, CD$_3$OD, ppm from TMS): 0.92 (3H, t); 1.02 (3H, s); 1.14 (3H, s); 3.05 (2H, m); 4.07 (1H, bs); 4.38 (2H, m); 6.91 (1H, bt).

EXAMPLE 8

E-17α-2-[(2-Aminoethoxy)iminomethyl]-5β-14,15-seco-3β-hydroxy-androstan-14-one oxalate (I-ao) and Z-17α-2-[(2-Aminoethoxy)iminomethyl]-5β-14,15-seco-3β-hydroxy-androstan-14-one oxalate (I-ap)

3β-Acetoxy-14,15-dioxo-17β-ethyl-14,15-seco-5β-androstane (II-b, Prep. 7) (3.0 g) was reacted with 2-aminoethoxyamine dihydrochloride (1.1 g) as described in Ex. 1; the pure Z and E compounds obtained by flash-chromatography were reacted with the stoichiometric equivalent of oxalic acid in diethyl ether to give 1.3 g of the E isomer (I-ao) and 0.2 g of the Z isomer (I-ap) as white solids.

E isomer (I-ao) $^1$H-NMR (300 MHz, CD$_3$OD, ppm from TMS): 0.94 (3H, t); 1.05 (3H, s); 1.17 (3H, s); 3.20 (2H, m); 4.02 (1H, bs); 4.18 (2H, m); 7.60 (1H, bt).

Z isomer (I-ap) $^1$H-NMR (300 MHz, CD$_3$OD, ppm from TMS): 0.94 (3H, t); 1.05 (3H, s); 1.17 (3H, s); 3.20 (2H, m); 4.02 (1H, bs); 4.25 (2H, m); 6.93 (1H, bt).

EXAMPLE 9

E-17β-2-[(2-Dimethylaminoethoxy)iminomethyl]-5β-14,15-seco-3β-hydroxy-androstan-14-one oxalate (I-aq) and Z-17β-2-[(2-Dimethylaminoethoxy)iminomethyl]-5β-14,15-seco-3β-hydroxy-androstan-14-one oxalate (I-ar)

3β-Acetoxy-14,15-dioxo-17α-ethyl-14,15-seco-5β-androstane (II-d, Prep. 9) (3.15 g) was reacted with 2-dimethylaminoethoxyamine dihydrochloride (1.3 g) as described in Ex. 1; the pure Z and E compounds obtained by flash-chromatography were reacted with the stoichiometric equivalent of oxalic acid in diethyl ether to give 1.7 g of the E isomer (I-aq) and 0.5 g of the Z isomer (I-ar) as white solids.

E isomer (I-aq) $^1$H-NMR (300 MHz, CD$_3$OD, ppm from TMS): 0.92 (3H, t); 1.02 (3H, s); 1.14 (3H, s); 2.64 (1H, m); 2.96 (6H, s); 348 (2H, m); 4.02 (1H, bs); 4.32 (2H, m); 7.63 (1H, t).

Z isomer (I-ar) $^1$H-NMR (300 MHz, CD$_3$OD, ppm from TMS): 0.92 (3H, t); 1.02 (3H, s); 1.14 (3H, s); 2.96 (6H, s); 3.48 (2H, m); 4.38 (2H, m); 6.91 (1H, t).

EXAMPLE 10

E-17α-2-[(2-Dimethylaminoethoxy)iminomethyl]-
5β-14,15-seco-3β-hydroxy-androstan-14-one
oxalate (I-as) and Z-17β-2-[(2-
Dimethylaminoethoxy)iminomethyl]-5β-14,15-seco-
3β-hydroxy-androstan-14-one oxalate (I-at)

3β-Acetoxy- 14,15-dioxo-17p-ethyl-14,15-seco-5,-androstane (II-b, Prep. 7) (3.4 g) was reacted with 2-dimethylaminoethoxyamine dihydrochloride (1.4 g) as described in Ex. 1: the pure Z and E compounds obtained by flash-chromatography were reacted with the stoichiometric equivalent of oxalic acid in diethyl ether to give 1.4 g of the E isomer (I-as) and 0.4 g of the Z isomer (I-at) as white solids.

E isomer (I-as) $^1$H-NMR (300 MHz, CDCl$_3$, ppm from TMS): 0.92 (3H, t); 1.04 (3H, s); 1.12 (3H, s); 2.90 (6H, s); 3.36 (2H, m); 4.10 (1H, bs); 4.38 (2H, m); 7.50 (1H, bt).

Z isomer (I-at) $^1$H-NMR (300 MHz, CDCl$_3$, ppm from TMS): 0.92 (3H, t); 1.04 (3H, s); 1.16 (3H, s); 2.90 (6H, s); 3.49 (2H, m); 4.10 (1H, bs); 4.44 (2H, m); 6.88 (1H, bt).

EXAMPLE 11

E-17α-2-[(2-Aminoethoxy)iminomethyl]-5β-14,15-
seco-3β,14β-dihydroxy-androstan oxalate (I-au)

To a solution of E-17α-2-[(2-aminoethoxy)iminoethyl]-5β-14,15-seco-3βhydroxy-androstan-14-one free base (prepared as described in Ex. 8) (5.0 g) in MEOH (250 mL) kept at −30° C., NaBH$_4$ (1.3 g) was added dropwise. After 12 hrs the reaction mixture was poured in a chilled 10% ACOH aqueous solution, and the mixture extracted with CHCl$_3$. The organic layer was dried over anhydrous sodium sulfate and evaporated to dryness under reduced pressure. The residue was purified by chromatography (SiO$_2$) using CHCl$_3$:MeOH:NH$_4$OH 98/2/0.25 as eluant, to give the pure compound that was reacted with the stoichiometric equivalent of oxalic acid in methanol, to give 1.4 g of the title compound (I-au) as a white solid.

$^1$H-NMR (300 MHz, CD$_3$OD, ppm from TMS): 0.92 (3H, t); 1.04 (3H, s); 1.07 (3H, s); 3.20 (2H, m); 3.26 (1H, d); 4.02 (1H, bs); 4.23 (2H, m); 7.61 (1H, bt).

EXAMPLE 12

E-17α-2-[(2-Aminoethoxy)iminomethyl]-5β-14,15-
seco-3β,14β-dihydroxy-androstan oxalate (I-av)

Z-17α-2-[(2-aminoethoxy)iminoethyl]-5p- 14,15-seco-3β-hydroxy-androstan-14-one free base (prepared as described in Ex. 8) (2.0 g) was reacted with NaBH$_4$ (0.7 g) and then with the stoichiometric equivalent of oxalic acid, as described in Ex. 11 to give 0.5 g of the title compound (I-av) as a white solid.

$^1$H-NMR (300 MHz, CD$_3$OD, ppm from TMS): 0.92 (3H, t); 1.04 (3H, s); 1.07 (3H, s); 3.20 (2H, m); 3.33 (1H, d); 4.02 (1H, bs); 4.23 (2H, m); 6.89 (1H, bt).

EXAMPLE 13

E-17α-2-[(2-Dimethylaminoethoxy)iminomethyl]-
5β-14,15-seco-3β,14β-dihydroxy-androstan oxalate
(I-aw)

E-17α-2-[(2-Dimethylaminoethoxy)iminoethyl]-5β-14,15-seco-3β-hydroxy-androstan-14-one free base (prepared as described in Ex. 10) (4.0 g) was reacted with NaBH$_4$ (1.2 g) and then with the stoichiometric equivalent of oxalic acid, as described in Ex. 11, to give 1.2 g of the title compound (I-aw) as a white solid.

$^1$H-NMR (300 MHz, CDCl$_3$, ppm from TMS): 0.92 (3H, t); 1.05 (3H, s); 1.07 (3H, s); 2.91 (6H, s); 3.25 (1H, d); 3.44 (2H, m); 4.12 (1H, bs); 4.37 (2H, m); 7.44 (1H, bt).

EXAMPLE 14

E-17α-2-[(2-Dimethylaminoethoxy)iminomethyl]-
5β-14,15-seco-3β,14β-dihydroxy-androstan oxalate
(I-ax) Z-17α-2-[(2-Dimethylaminoethoxy)
iminoethyl]-5β-14,15-seco-3β-hydroxy-androstan-
14-one free base (prepared as described in Ex. 10)
(2.0 g) was reacted with NaBH$_4$ (0.75 g) and then
with the stoichiometric equivalent of oxalic acid, as
described in Ex. 11 to give 0.6 g of the title
compound (I-ax) as a white solid.

$^1$H-NMR (300 MHz, CDCl$_3$, ppm from TMS): 0.92 (3H, t); 1.04 (3H, s); 1.06 (3H, s); 2.91 (6H, s); 3.20 (1H, d); 3.45 (2H, m); 4.10 (1H, bs); 4.35 (2H, m); 6.75 (1H, bt).

EXAMPLE 15

E-17α-2-(2-Guanidinoiminoethyl)-5β-14,15-seco-
3β-hydroxy-androstan-14-one oxalate (I-ay) and Z-
17α-2-(2-Guanidinoiminoethyl)-5β-14,15-seco-3β-
hydroxy-androstan-14-one oxalate (I-az)

3β-Acetoxy-14,15-dioxo-17β-ethyl-14,15-seco-5β-androstane (II-b, Prep. 7) (4.0 g) was reacted with aminoguanidine bicarbonate (1.7 g) as described in Ex. 1: the pure Z and E compounds obtained by flash-chromatography were reacted with the stoichiometric equivalent of oxalic acid in diethyl ether to give 2.4 g of the E isomer (I-ay) and 0.4 g of the Z isomer (I-az) as white solids.

E isomer (I-ay) $^1$H-NMR (300 MHz, CD$_3$OD, ppm from TMS): 0.93 (3H, t); 1.05 (3H, s); 1.18 (3H, s); 4.01 (1H, bs); 7.55 (1H, bt).

Z isomer (I-az) $^1$H-NMR (300 MHz, CD$_3$OD, ppm from TMS): 0.93 (3H, t); 1.06 (3H, s); 1.18 (3H, s); 4.01 (1H, bs); 7.03 (1H, bt).

EXAMPLE 16

E-17β-Propyl-15-[(2-aminoethoxy)imino]-5β-14,15-
seco-3β-hydroxy-androstan-14-one oxalate (I-ba)
and Z-17β-Propyl-15-[(2-aminoethoxy)imino]-5β-
14,15-seco-3β-hydroxy-androstan-14-one oxalate (I-
bb)

3β-t-Butyldimethylsilyloxy-14,15-dioxo-17β-propyl-14,15-seco-5β-androstane (II-g, Prep. 12) (3.2 g) was reacted with 2-aminoethoxyamine dihydrochloride (1.1 g) as described in Ex. 1, but using diluted HCl in ethanol for cleaving the silyloxy protective group; the pure Z and E compounds obtained by flash-chromatography were reacted with the stoichiometric equivalent of oxalic acid in diethyl ether to give 1.1 g of the E isomer (I-ba) and 1.0 g of the Z isomer (I-bb) as white solids.

E isomer (I-ba) $^1$H-NMR (300 MHz, CD$_3$OD, ppm from TMS): 0.89 (3H, m); 1.05 (3H, s); 1.17 (3H, s); 2.20–2.70 (3H, m); 3.12 (2H, m); 4.02 (1H, s); 4.19 (2H, m); 7.58 (1H, m).

Z isomer (I-bb) $^1$H-NMR (300 MHz, CD$_3$OD, ppm from TMS): 0.89 (3H, m); 1.05 (3H, s); 1.17 (3H, s); 2.20–2.70 (3H, m); 3.12 (2H, m); 4.02 (1H, s); 4.26 (2H, m); 6.90 (1H, m).

EXAMPLE 17

E-17β-Propyl-15-[(2-dimethylaminoethoxy)imino]-5β-14,15-seco-3β-hydroxy-androstan-14-one oxalate (I-bc) and Z-17β-Propyl-15-[(2-dimethylaminoethoxy)imino]-5β-14,15-seco-3β-hydroxy-androstan-14-one oxalate (I-bd)

3β-t-Butyldimethylsilyloxy-14,15-dioxo-17β-propyl-14,15-seco-5β-androstane (II-g, Prep. 12) (2.0 g) was reacted with 2-dimethylaminoethoxyamine dihydrochloride (1.2 g) as described in Ex. 1, but using diluted HCl in ethanol for cleaving the silyloxy protective group; the pure Z and E compounds obtained by flash-chromatography were reacted with the stoichiometric equivalent of oxalic acid in diethyl ether to give 0.8 g of the E isomer (I-ba) and 0.5 g of the Z isomer (I-bb) as white solids.

E isomer (I-ba) $^1$H-NMR (300 MHz, CD$_3$OD, ppm from TMS): 0.89 (3H, m); 1.05 (3H, s); 1.17 (3H, s); 2.20–2.70 (3H, m); 2.81 (6H, s); 3.02 (2H, m); 4.00 1H, s); 4.15 (2H, m); 7.55 (1H, m).

Z isomer (I-bb) $^1$H-NMR (300 MHz, CD$_3$OD, ppm from TMS): 0.89 (3H, m);

1.05 (3H, s); 1.17 (3H, s); 2.20–2.70 (3H, m); 2.75 (6H, s); 3.05 (2H, m); 4.01 (1H, s); 4.29 (2H, m); 6.92 (1H, m).

EXAMPLE 18

E,E-17α-4-[(2-Dimethylaminoethoxyimino)-2-butenyl]-5β-14,15-seco-3β-hydroxy-androstan-14-one oxalate (I-be) and E,Z-17α-4-[(2-Dimethylaminoethoxyimino)-2-butenyl]-5β-14,15-seco-3β-hydroxy-androstan-14-one oxalate (I-bf)

To a solution of E,Z-(EtO)$_2$POCH$_2$CH=NOCH$_2$CH$_2$NMe$_2$ (3.0 g) in toluene (100 mL) kept at −78° C. and under nitrogen, BuLi (7.2 mL) was added dropwise; the reaction mixture was stirred at the same temperature for 1 hr and then allowed to rise to room temperature. To this solution 3β-acetoxy-14,15-dioxo-17β-ethyl-14,15-seco-5β-androstane (II-b, Prep. 7) (3.5 g, dissolved in 50 mL of toluene) was added dropwise. The reaction mixture was stirred at room temp. for 20 hrs, then poured in a saturated aqueous solution of NH$_4$Cl and the mixture extracted with EtOAc. The organic layer was dried over anhydrous sodium sulfate and evaporated to dryness under reduced pressure. The residue was purified by chromatography (SiO$_2$) using CHC$_3$:MeOH:NH$_4$OH 98/2/0.25 as eluant to give 2.7 g of the 3β-acetoxy derivatives of the title compounds. The 3β-acetoxy derivatives were dissolved in a mixture of MeOH/water (130/30 mL) and K$_2$CO$_3$ (8.2 g) was added. The reaction mixture was stirred at room temperature for 20 hrs, then poured in a saturated aqueous solution of NH$_4$Cl and the mixture extracted with EtOAc. The organic layer was dried over anhydrous sodium sulfate and evaporated to dryness under reduced pressure. The E,E and E,Z Isomers were separated by chromatography (SiO$_2$) using CHCl$_3$:MeOH:NH$_4$OH 98/2/0.25 as eluant to give the pure E,E and E,Z compounds that were reacted with the stoichiometric equivalent of oxalic acid in diethyl ether to give 1.1 g of the E,E isomer (I-be) and 1.0 g of the E,Z isomer (I-bf) as white solids.

E,E isomer (I-be) $^1$H-NMR (300 MHz, CD$_3$OD, ppm from TMS): 0.82 (3H, t);

1.04 13H, s); 1.17 (3H, s); 2.94 (6H, s); 3.48 (2H, m); 4.01 (1H, bs); 4.37 (2H, m); 6.15 (1H, dd); 6.83 (1H, m); 7.84 (1H, d).

E,Z isomer (I-bf) $^1$H-NMR (300 MHz, CD$_3$OD, ppm from TMS): 0.82 (3H, t); 1.04 (3H, s); 1.17 (3H, s); 2.94 (6H, s); 3.48 (2H, m); 4.01 (1H, bs); 4.37 (2H, m); 6.70 (1H, dd); 6.83 (1H, m); 7.18 (1H, d).

EXAMPLE 19

E-17α-2-[(2-Aminoethoxy)iminomethyl]-14,15-seco-3β-hydroxy-androstan-14-one oxalate (I-bg) and Z-17α-2-[(2-Aminoethoxy)iminomethyl]-14,15-seco-3β-hydroxy-androstan-14-one oxalate (I-bh)

3β-Acetoxy-14,15-dioxo-17β-ethyl-14,15-seco-androstane (II-f, Prep. 11) (3.4 g) was reacted with 2-aminoethoxyamine dihydrochloride (1.7 g) as described in Ex. 1: the pure Z and E compounds obtained by flash-chromatography were reacted with the stoichiometric equivalent of oxalic acid in diethyl ether to give 0.7 g of the E isomer (I-bg) and 0.4 g of the Z isomer (I-bh) as white solids.

E isomer (I-bg) $^1$H-NMR (300 MHz, CD$_3$OD, ppm from TMS): 0.89 (3H, s); 1.15 (3H, s); 3.21 (2H, m); 4.20 (2H, t); 7.59 (1H, dd).

Z isomer (I-bh) $^1$H-NMR (300 MHz, CD$_3$OD, ppm from TMS): 0.89 (3H, s); 1.15 (3H, s); 3.52 (2H, m); 4.26 (2H, t); 6.92 (1H, t).

EXAMPLE 20

E-17α-2-[(2-Dimethylaminoethoxy)iminomethyl]-14,15-seco-3β-hydroxy-androstan-14-one oxalate (I-bi) and Z-17α-2-[(2-Dimethylaminoethoxy)iminomethyl]-14,15-seco-3β-hydroxy-androstan-14-one oxalate (I-bj)

3β-Acetoxy-14,15-dioxo-17β-ethyl-14,15-seco-androstane (II-f, Prep. 11) (3.0 g) was reacted with 2-dimethylaminoethoxyamine dihydrochloride (1.7 g) as described in Ex. 1: the pure Z and E compounds obtained by flash-chromatography were reacted with the stoichiometric equivalent of oxalic acid in diethyl ether to give 0.8 g of the E isomer (I-bi) and 0.3 g of the Z isomer (I-bj) as white solids.

E isomer (I-bi) $^1$H-NMR (300 MHz, DMSO-d$_6$, ppm from TMS): 0.82 (3H, s); 1.05 (3H, s); 3.22 (2H, m); 4.22 (2H, m); 7.52 (1H, m).

Z isomer (I-bj) $^1$H-NMR (300 MHz, DMSO-d$_6$, ppm from TMS): 0.82 (3H, s); 1.05 (3H, s); 3.32 (2H, m); 4.27 (2H, t); 6.92 (1H, m).

EXAMPLE 21

E-17α-(2-Guanidinoiminoethyl)-14,15-seco-3β-hydroxy-androstan-14-one oxalate (I-bk) and Z-17α-(2-Guanidinoiminoethyl)-14,15-seco-3β-hydroxy-androstan-14-one oxalate (I-bl)

3β-Acetoxy-14,15-dioxo-17β-ethyl-14,15-seco-androstane (II-f, Prep. 11) (2.0 g) was reacted with aminoguanidine sulfate (2.0 g) as described in Ex. 1; the pure Z and E compounds obtained by flash-chromatography were reacted with the stoichiometric equivalent of oxalic acid in methanol to give 0.8 g of the E isomer (I-bk) and 0.3 g of the Z isomer (I-bl) as white solids.

E isomer (I-bk) $^1$H-NMR (300 MHz, CD$_3$OD, ppm from TMS): 0.88 (3H, s); 1.18 (3H, s); 3.51 (1H, m); 7.53 (1H, t).

Z isomer (I-bl) $^1$H-NMR (300 MHz, CD$_3$OD, ppm from TMS): 0.88 (3H, s); 1.18 (3H, s); 3.51 (1H, m); 7.01 (1H, t).

PREPARATION 1

3β-Acetoxy-17β-methyl-5β-androst-14-ene (VII-a)

A solution of 9.1 g of 3β,14β-dihydroxy-5β-androstane-17β-carboxaldehyde (Boutagy J. and Thomas R., *Aust. J. Chem.*, 1971, 24, 2723), and p-toluensulphonyl hydrazide (5.6 g) in AcOH (60 mL) was stirred at room temp. for 3 hrs and then poured in a saturated aqueous solution of di-sodium hydrogen phosphate. The mixture was extracted with ethyl acetate, the organic layer was dried over anhydrous sodium sulfate and evaporated to dryness under reduced pressure. The residue was dissolved in MeOH (200 mL) and zinc iodide (1.2 g) was added. To this solution sodium cyanoborohydride (2.6 g) was added portionwise and the temperature was raised to the boiling point of the reaction mixture. After 3 hrs the solvent was evaporated to dryness under reduced pressure, the crude product was dissolved in ethyl acetate and neutralised with 0.1 N NaOH, the organic layer was dried over anhydrous sodium sulfate and evaporated to dryness under reduced pressure. The residue was purified by chromatography (SiO$_2$) using n-hexane/ethyl ether 75/25 as eluant to give 5.7 g of 3β-acetoxy-14β-hydroxy-17β-methyl-5β-androstane (VIII-a) as a white solid.

$^1$H-NMR (300 MHz, CDCl$_3$, ppm from TMS): 0.92 (3H, s); 0.96 (3H, s); 1.03 (3H, d); 2.05 (3H, s); 5.04 (1H, bs).

To a solution of 5.0 g of 3β-acetoxy-14β-hydroxy-17β-methyl-5β-androstane (VIII-a) in pyridine (100 mL), 3.5 g of thionyl chloride were added at 0° C. The solution was stirred at the same temperature for 2.5 hrs and then poured in 100 mL of 1N HCl and crushed ice: the mixture was extracted with ethyl ether: the organic layer was washed with a saturated aqueous solution of disodium hydrogen phosphate, dried over anhydrous sodium sulfate and evaporated to dryness under reduced pressure to give 4.5 g of 3β-acetoxy-17β-methyl-5β-androst-14-ene as a white solid.

$^1$H-NMR (300 MHz, CDCl$_3$, ppm from TMS): 0.82 (3H, s); 0.96 (3H, d); 1.00 (3H, s); 2.06 (3H, s); 5.05 (1H, bs); 5.17 (1H, bs).

PREPARATION 2

3β-acetoxy-5β-pregn-14-ene (VII-b)

A solution of 27.4 g of 3β-acetoxy-5β-pregn-14-en-20-one (Bach, G. et al, *Can J. Chem.* 1968, 46, 733) and p-toluensulphonyl hydrazide (17.1 g) in AcOH (50 mL) was stirred at room temp. for 4 hrs. The solvent was evaporated to dryness under reduced pressure; the residue obtained was dissolved in MeOH (600 mL) and zinc iodide (3.0 g) was added. To this solution sodium cyanoborohydride (14.4 g) was added portionwise and the temperature was raised to the boiling point of the reaction mixture. After 4 hrs the solvent was evaporated to dryness under reduced pressure, the crude product was dissolved in ethyl acetate and neutralised with 0.1 N NaOH; the organic layer was dried over anhydrous sodium sulfate and evaporated to dryness under reduced pressure. The residue was purified by flash-chromatography (SiO$_2$) using n-hexane/ethyl acetate 95/5 as eluant to give 18.2 g of 3β-acetoxy-5β-pregn-14-ene as a white solid.

$^1$H-NMR (300 MHz, CDCl$_3$, ppm from TMS): 0.84 (3H, s); 0.92 (3H, t); 1.01 (3H, s); 2.06 (3H, s); 5.04 (1H, bs); 5.17 (1H, bs).

PREPARATION 3

3β-acetoxy-5β,17α-pregn-14-ene (VII-c)

A solution of 10.0 g of 3β-acetoxy-5β-pregn-14-en-20-one (Bach, G. et al. *Can. J. Chem.* 1968, 46, 733) and K$_2$CO$_3$ (25.0 g) in MeOH/water (160 mL/80 mL) was stirred at room temperature for 2 hrs; the organic solvent was evaporated to dryness under reduced pressure and the aqueous suspension obtained was extracted with CH$_2$Cl$_2$; the organic layer was dried over anhydrous sodium sulfate and evaporated to dryness under reduced pressure; the crude 3β-acetoxy-5β,17α-pregn-14-en-20-one obtained was used for the next step without further purification. A solution of the crude intermediate and p-toluensulphonyl hydrazide (11.1 g) in AcOH (300 mL) was stirred at room temp. for 12 hrs. To this solution NaBH$_4$ (7.8 g) was added portionwise; after 2 hrs the reaction mixture was poured in water/ice and the aqueous suspension obtained was extracted with AcOEt and neutralised with 0.1 N NaOH: the organic layer was dried over anhydrous sodium sulfate and evaporated to dryness under reduced pressure. The residue was purified by flash-chromatography (SiO$_2$) using n-hexane/ethyl acetate 1/1 as eluant to give 7.0 g of 3β-acetoxy-5β,17α-pregn-14-ene as a white solid.

$^1$H-NMR (300 MHz, CDCl$_3$, ppm from TMS): 0.90 (3H, t); 1.01 (3H, s); 1.06 (3H, s); 2.06 (3H, s); 2.54 (1H, m); 5.05 (1H, bs); 5.10 (1H, bs).

PREPARATION 4

3β-acetoxy-pregn-14-ene (VII-d)

A solution of 5.2 g of 3β-acetoxy-pregn-14-en-20-one (Gambara, T. et al, *Chem. Pharm. Bull.*, 1970, 18, 453) and p-toluensulphonyl hydrazide (3.5 g) in AcOH (50 mL) was stirred at room temp. for 3 hrs. The solvent was evaporated to dryness under reduced pressure: the residue obtained was dissolved in MeOH (200 mL) and zinc iodide (0.6 g) was added. To this solution sodium cyanoborohydride (1.5 g) was added portionwise and the temperature was raised to the boiling point of the reaction mixture. After 2 hrs the solvent was evaporated to dryness under reduced pressure, the crude product was dissolved in ethyl acetate and neutralised with 0.1 N NaOH; the organic layer was dried over anhydrous sodium sulfate and evaporated to dryness under reduced pressure. The residue was purified by flash-chromatography (SiO$_2$) using n-hexane/ethyl acetate 97/3 as eluant to give 3.7 g of 3β-acetoxy-pregn-14-ene as a white solid.

$^1$H-NMR (300 MHz, CDCl$_3$, ppm from TMS): 0.82 (3H, s); 0.86 (3H, s); 0.93 (3H, t); 2.05 (3H, s); 2.37 (3H, m); 4.69 (1H, m); 5.16 (1H, bs).

PREPARATION 5

3β-t-butyldimethylsilyloxy-17β-n-propyl-5β-androst-14-ene (VII-e)

To a solution of ethylmagnesium bromide in diethyl ether (3M, 100 mL) kept at room temp., was added dropwise a solution of 10.0 g of 3β-t-butyldimethylsilyloxy-14β-hydroxy-5β-androstane-17β-carboxaldehyde in 400 ml of toluene (prepared from the known 3β,14β-dihydroxy-5β-androstane-17β-carboxaldehyde: Boutagy J. and Thomas R., *Aust. J. Chem.*, 1971, 24, 2723), and the reaction mixture was stirred at room temp. for 2 hrs. The reaction mixture was then poured in a saturated, chilled solution of ammonium chloride and the suspension was extracted with EtOAc. The organic layer was dried over anhydrous sodium sulfate and evaporated to dryness to give the crude secondary alcohol 3β-t-butyldimethylsilyloxy-14β,20ζ-dihydroxy-17β-n-propyl-5β-androstane.

To a solution in THF (400 mL) of the crude secondary alcohol, NaH (4.7 g of 65% oily dispersion) was added portionwise and the reaction mixture was refluxed for 2 hrs. To this mixture carbon disulfide (13.0 mL) was added dropwise and after 30' methyl iodide (27.0 mL) was added dropwise. After 30' the reaction mixture was cooled to 0° C. and a saturated solution of ammonium chloride (200 mL) was added. The suspension was extracted with EtOAc and the organic layer was dried over anhydrous sodium sulfate and evaporated to dryness to give the crude thioderivative 3β-t-butyldimethylsilyloxy-14β-hydroxy-17β-n-propyl-20β-[(methylthio)thiocarbonyloxy)]-5β-androstane. A solution of the crude thioderivative, tris(trimethylsilyl)silane (12.0 mL) and AIBN (0.5 g) in toluene (400 mL) was refluxed for 2 hrs then other tris(trimethylsilyl)silane (5.0 mL) and AIBN (0.3 g) were added and the reaction refluxed for 1 hr. The reaction mixture was cooled to 0° C. and a saturated solution of sodium chloride (200 mL) was added. The suspension was extracted with EtOAc, the organic layer was dried over anhydrous sodium sulfate and evaporated to dryness to give the crude 3β-t-butyldimethylsllyloxy-14β-hydroxy- 17β-n-propyl-5β-androstane. To a solution of the crude 17β-n-propyl derivative, in pyridine (100 mL) kept at 0° C., thionyl chloride (2.4 mL) was added. The solution was stirred at 0° C. for 2.5 hrs and then poured in 100 mL of 1N HCl and crushed ice. The mixture was extracted with ethyl ether, the organic layer was washed with a saturated aqueous solution of di-sodium hydrogen phosphate, dried over anhydrous sodium sulfate and evaporated to dryness under reduced pressure to give 3.5 g of 3β-t-butyldimethylsilyloxy-17β-n-proyl-5β-androst-14-ene as a white solid.

$^1$H-NMR (300 MHz, CDCl$_3$, ppm from TMS): 0.02 (6H, s); 0.83 (3H, d); 0.86 (12H, m); 0.92 (3H, s); 2.32 (1H, m); 4.00 (1H, s); 5.16 (1H, m).

PREPARATION 6

3β-Acetoxy-14,15-dioxo-17β-methyl-14,15-seco-5β-androstane (II-a)

A solution of 7.0 g of 3β-acetoxy-17β-methyl-5β-androst-14-ene (VII-a) in methylene chloride (400 mL) was cooled at −78° C. and a stream of ozone was passed through until the reaction was complete (ca 1 h). The excess of ozone was removed by a stream of nitrogen, then zinc (30.0 g) and AcOH (45.0 mL) were slowly added and the temperature was allowed to rise to room temperature. After 3 hrs stirring the mixture was filtered, the solid was washed with CH$_2$Cl$_2$ and the solution was evaporated to dryness under reduced pressure. The residue was dissolved in EtOAc and washed with a saturated aqueous solution of di-sodium hydrogen phosphate: the organic layer was dried over anhydrous sodium sulfate and evaporated to dryness to give 7.8 g of 3β-acetoxy-14,15-dioxo-17β-methyl-14,15-seco-5β-androstane as a white solid.

$^1$H-NMR (300 MHz, CDCl$_3$, ppm from TMS): 0.84 (3H, d); 1.07 (3H, s); 1.12 (3H, s); 2.05 (3H, s); 5.05 (1H, m); 9.78 (1H, t).

PREPARATION 7

3β-Acetoxy- 14,15-dioxo-17β-ethyl-14,15-seco-5β-androstane (II-b)

A solution of 16.0 g of 3β-acetoxy-5β-pregn-14-ene (VII-b) in methylene chloride (800 mL) was cooled at −78° C. and a stream of ozone was passed through until the reaction was complete (ca 1 h). The excess of ozone was removed by a stream of nitrogen, then zinc (63.0 g) and AcOH (90.0 mL) were slowly added and the temperature was allowed to rise to room temperature. After 3 hrs stirring the mixture was filtered, the solid was washed with CH$_2$Cl$_2$ and the solution was evaporated to dryness under reduced pressure. The residue was dissolved in EtOAc and washed with a saturated aqueous solution of di-sodium hydrogen phosphate; the organic layer was dried over anhydrous sodium sulfate and evaporated to dryness to give 17.1 g of 3β-acetoxy-14,15-dioxo- 17β-ethyl-14,15-seco-5β-androstane as a white solid.

$^1$H-NMR (300 MHz, CDCl$_3$, ppm from TMS): 0.90 (3H, t); 1.04 (3H, s); 1.12 (3H, s); 2.06 (3H, s); 5.06 (1H, m); 9.82 (1H, t).

PREPARATION 8

3β-Acetoxy-14-oxo-17α-formyl-14,15-seco-5β-androstane (II-c)

A solution of 30.4 g of 3β-acetoxy-14,15-dioxo-17β-ethyl-14,15-seco-5β-androstane (II-b), Ac$_2$O (94.0 mL), TEA (94.0 mL) and DMAP (1.0 g) in methylene chloride (400 mL) was stirred at room temp. for 8 hrs. The excess of AC20 was decomposed with EtOH (100 mL) and the solution was poured in water/crushed ice. The mixture was extracted with ethyl ether, the organic layer was washed with a 5% aqueous solution of NaHCO$_3$, dried over anhydrous sodium sulfate and evaporated to dryness. The residue was purified by flash-chromatography (SiO$_2$) using n-hexane/ethyl ether 90/10 to 80/20 as eluant to give 17.5 g of the enol acetate. A solution of 17.0 g of enol acetate in methylene chloride (500 mL) was cooled at −78° C. and a stream of ozone was passed through until the reaction was complete (ca 1 h). The excess of ozone was removed by a stream of nitrogen, then dimethyl sulfide (6.0 mL) was added dropwise and the temperature was allowed to rise to room temperature. After 48 hrs stirring the solution was evaporated to dryness under reduced pressure and the residue was purified by flash-chromatography (SiO$_2$) using n-hexane/ethyl acetate 80/20 as eluant to give 13.1 g of 3β-acetoxy-14-oxo-17α-formyl-14,15-seco-5β-androstane as a white solid.

$^1$H-NMR (300 MHz, CDCl$_3$, ppm from TMS): 0.94 (3H, t); 1.06 (3H, s); 1.30 (3H, s); 2.09 (3H, s); 5.03 (1H, bs); 9.90 (1H, t).

PREPARATION 9

3β-Acetoxy-14,15-dioxo-17α-ethyl-14,15-seco-5β-androstane (II-d)

A solution of 10.0 g of 3β-acetoxy-5β,17α-pregn-14-ene (VII-c) in methylene chloride (200 mL) was cooled at −78° C. and a stream of ozone was passed through until the reaction was complete (ca 1 h). The excess of ozone was removed by a stream of nitrogen, then zinc (200 g) and AcOH (300 mL) were slowly added and the temperature was allowed to rise to room temperature. After 3 hrs stirring the mixture was filtered, the solid was washed with CH$_2$Cl$_2$ and the solution was evaporated to dryness under reduced pressure. The residue was dissolved in EtOAc and washed with a saturated aqueous solution of di-sodium hydrogen phosphate: the organic layer was dried over anhydrous sodium sulfate and evaporated to dryness to give 9.2 g of 3β-acetoxy-14,15-dioxo-17α-ethyl-14,15-seco-5β-androstane as a white solid.

¹H-NMR (300 MHz, CDCl₃, ppm from TMS): 0.92 (3H, t); 1.03 (3H, s); 1.18 (3H, s); 2.06 (3H, s); 2.56 (1H, m); 5.05 (1H, bs); 9.76 (1H, bs).

PREPARATION 10

3β-Acetoxy-14-oxo-17β-formyl-14,15-seco-5β-androstane (II-e)

A solution of 5.0 g of 3β-acetoxy-14,15-dioxo-17α-ethyl-14,15-seco-5β-androstane (II-d), Ac₂O (16.1 mL), TEA (16.1 mL) and DMAP (0.4 g) in methylene chloride (100 mL) was stirred at room temp. for 9 hrs. The excess of Ac₂O was decomposed with EtOH (15 mL) and the solution was poured in water/crushed ice. The mixture was extracted with ethyl ether, the organic layer was washed with a 5% aqueous solution of NaHCO₃, dried over anhydrous sodium sulfate and evaporated to dryness. The residue was purified by flash-chromatography (SiO₂) using n-hexane/ethyl ether 90/10 to 80/20 as eluant to give 3.1 g of the enol acetate. A solution of 3.0 g of the enol acetate in methylene chloride (25 mL) was cooled at -78° C. and a stream of ozone was passed through until the reaction was complete (ca 1 h). The excess of ozone was removed by a stream of nitrogen, then dimethyl sulfide (1.7 mL) was added dropwise and the temperature was allowed to rise to room temperature. After 48 hrs stirring the solution was evaporated to dryness under reduced pressure and the residue was purified by flash-chromatography (SiO₂) using n-hexane/ethyl acetate 80/20 as eluant to give 2.0 g of 3β-acetoxy-14-oxo-17β-formyl-14,15-seco-5β-androstane as a white solid.

¹H-NMR (300 MHz, CDCl₃, ppm from TMS): 0.94 (3H, t);, 1.05 (3H, s); 1.15 (3H, s); 2.12 (3H, s); 5.06 (1H, bs); 9.87 (1H, t).

PREPARATION 11

3β-Acetoxy-14,15-dioxo-17β-ethyl-14,15-seco-androstane (II-f)

A solution of 2.0 g of 3β-acetoxy-pregn-14-ene (VII-d) in methylene chloride (200 mL) was cooled at -78° C. and a stream of ozone was passed through until the reaction was complete (ca 20'). The excess of ozone was removed by a stream of nitrogen, then zinc (7.6 g) and AcOH (11.0 mL) were slowly added and the temperature was allowed to rise to room temperature. After 3 hrs stirring the mixture was filtered, the solid was washed with CH₂Cl₂ and the solution was evaporated to dryness under reduced pressure. The residue was dissolved in EtOAc and washed with a saturated aqueous solution of di-sodium hydrogen phosphate; the organic layer was dried over anhydrous sodium sulfate and evaporated to dryness to give 1.1 g of 3β-acetoxy-14,15-dioxo-17β-ethyl-14,15-seco-androstane as a oil.

¹H-NMR (300 MHz, CDCl₃, ppm from TMS): 0.86 (6H, t); 1.08 (3H, s); 2.03 (3H, s); 4.69 (1H, m); 9.81 (1H, t).

PREPARATION 12

3β-t-Butyldimethylsilyloxy-14,15-dioxo-17β-n-propyl- 14,15-seco-5β-androstane (II-g)

A solution of 3.3 g of 3β-t-butyldimethylsilyloxy-17β-n-propyl-5β-androst-14-ene (VII-e) in methylene chloride (300 mL) was cooled at -78° C. and a stream of ozone was passed through until the reaction was complete (ca 20'). The excess of ozone was removed by a stream of nitrogen, then zinc (27.0 g) and ACOH (25.0 mL) were slowly added and the temperature was allowed to rise to room temperature. After 3 hrs stirring the mixture was filtered, the solid was washed with CH₂Cl₂ and the solution was evaporated to dryness under reduced pressure. The residue was dissolved in EtOAc and washed with a saturated aqueous solution of di-sodium hydrogen phosphate; the organic layer was dried over anhydrous sodium sulfate and evaporated to dryness to give 3.2 g of 3β-t-butyldimethylsilyloxy-14,15-dioxo-17β-propyl-14,15-seco-5β-androstane as an oil.

¹H-NMR (300 MHz, CDCl₃, ppm from TMS): 0.02 (6H, s); 0.88 (9H, s); 1.00 (3H, s); 1.08 (3H, s); 2.00–2.60 (3H, m); 4.03 (1H, s); 9.80 (1H, bs).

We claim:
1. Seco-D steroids derivatives of general formula (I):

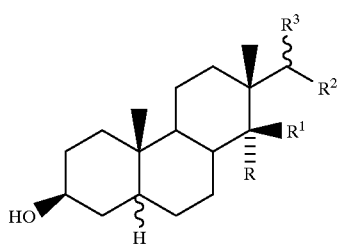

(I)

wherein:
the symbol ⁓ means that the hydrogen in position 5 and the substituent R³ in positon 17 can have an α or β configuration;
R and R¹ are respectively hydrogen and hydroxy, or R and R¹ taken together form a keto group;
R² is C₁–C₄ alkyl;
R³ is (CH₂)₀₋₁—CH=N ⁓ R⁴ or CH₂—CH=CH—CH=N ⁓ R⁴;
wherein
the symbol ⁓ means that both the Z isomer and the E isomer are considered;
R⁴ is NHC(=NH)NR⁵R⁶ or OR⁷;
wherein
R⁵, R⁶ are independently hydrogen, C1–C4 alkyl or R⁵ and R⁶ taken together form, with the nitrogen they are linked to, a saturated five o six membered monoheterocyclic ring;
R⁷ is hydrogen, C1–C6 alkyl, unsubstituted or substituted by NR⁸R⁹;
wherein
R⁸, R⁹ are independently hydrogen or C1–C4 alkyl.

2. Stereoisomers, Z and E isomers, tautomers, optical isomers and mixtures thereof and pharmaceutically acceptable salts of compounds of general formula (I) of claim 1.

3. A compound according to claim 1, which is selected from:
E-17β-2-[(2-Aminoethoxy)iminomethyl]-5β-14,15-seco-3β-hydroxy-androstan-14-one
E-17α-2-[(2-Aminoethoxy)iminomethyl]-5β- 14,15-seco-3β-hydroxy-androstan-14-one
E-17β-Methyl-15-[(2-aminoethoxy)imino]-5β- 14,15-seco-3β-hydroxy-androstan-14-one
E-17β-Methyl-15-[(2-dimethylaminoethoxy)imino]-5β-14,15-seco-3β-hydroxy-androstan-14-one E-17β-2-[(2-Dimethylaminoethoxy)iminomethyl]-5β-14,15-seco-3β-hydroxy-androstan-14-one
E-17α-2-[(2-Dimethylaminoethoxy)iminomethyl]-5β-14,15-seco-3β-hydroxy-androstan-14-one
E-17β-2-[(2-Aminoethoxy)iminoethyl]-5β-14,15-seco-3β-hydroxy-androstan-14-one
E-17α-2-[(2-Aminoethoxy)iminoethyl]-5β-14,15-seco-3β-hydroxy-androstan-14-one
E-17β-2-[(2-Dimethylaminoethoxy)iminoethyl]-5β-14,15-seco-3β-hydroxy-androstan-14-one
E-17α-2-[(2-Dimethylaminoethoxy)iminoethyl]-5β-14,15-seco-3β-hydroxy-androstan-14-one
E-17α-2-[(2-Aminoethoxy)iminoethyl]-5β-14,15-seco-3β,14β-dihydroxy-androstane
E-17α-2-[(2-Dimethylaminoethoxy)iminoethyl]-5β-14,15-seco-3β,14β-dihydroxy-androstane
E-17α-(2-Guanidinoiminoethyl)-5β-14,15-seco-3β-hydroxy-androstan-14-one
E-17β-Propyl-15-[(2-aminoethoxy)imino]-5β-14,15-seco-3β-hydroxy-androstan-14-one
E-17β-Propyl-15-[(2-dimethylaminoethoxy)imino]-5β-14,15-seco-3β-hydroxy-androstan-14-one
E,E-17α-4-[(2-Dimethylaminoethoxyimino)-2-butenyl]-5β-14,15-seco-3β-hydroxy-androstan-14-one
E-17α-2-[(2-Aminoethoxy)iminoethyl]-14,15-seco-3β-hydroxy-androstan-14-one
E-17α-2-[(2-Dimethylaminoethoxy)iminoethyl]-14,15-seco-3β-hydroxy-androstan-14-one
E-17α-(2-Guanidinoiminoethyl)-14,15-seco-3β-hydroxy-androstan-14-one.

4. A process for the preparation of said compounds of general formula I of claim 1 which comprises the condensation reaction of a compound of general formula II

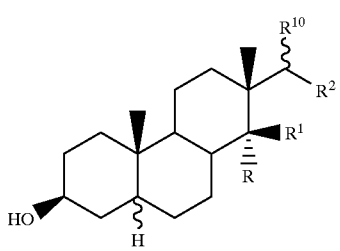

II in which: the symbol ⁓ and the substituent $R^2$ is as above defined, R and $R^1$ form a keto group and $R^{10}$ is CHO or $CH_2$—CHO with a compound of general formula (III), (IV), (V) or (VI)

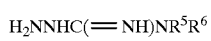

III $H_2NNHC(\!\!=\!\!NH)NR^5R^6$

IV $H_2NOR^7$

V $(EtO)_2POCH_2$—CH=NH—NHC(=NH)NR^5R^6

VI $(EtO)_2POCH_2$—CH=NOR^7 to give compounds of general formula I of claim 1 where $R^3$, $R^5$, $R^6$, $R^7$ is as defined above in claim 1.

5. A pharmaceutical composition containing a compound of general formula I with a pharmaceutically acceptable carrier and/or diluent.

6. A compound according to claim 1, which is selected from:

Z-17β-2-[(2-Aminoethoxy)iminomethyl]-5β-14,15-seco-3β-hydroxy-androstan-14-one;
Z-17α-2-[(2-Aminoethoxy)iminomethyl]-5β-14,15-seco-3β-hydroxy-androstan-14-one;
Z-17β-Methyl-15-[(2-aminoethoxy)imino]-5β-14,15-seco-3β-hydroxy-androstan-14-one;
Z-17β-Methyl-15-[(2-dimethylaminoethoxy)imino]-5β-14,15-seco-3β-hydroxy-androstan-14-one;
Z-17β-2-[(2-Dimethylaminoethoxy)iminomethyl]-5β-14,15-seco-3β-hydroxy-androstan-14-one;
Z-17α-2-[(2-Dimethylaminoethoxy)iminomethyl]-5β-14,15-seco-3β-hydroxy-androstan-14-one;
Z-17β-2-[(2-Aminoethoxy)iminoethyl]-5β-14,15-seco-3β-hydroxy-androstan-14-one;
Z-17α-2-[(2-Aminoethoxy)iminoethyl]-5β-14,15-seco-3β-hydroxy-androstan-14-one;
Z-17β-2-[(2-Dimethylaminoethoxy)iminoethyl]-5β-14,15-seco-3β-hydroxy-androstan-14-one;
Z-17α-2-[(2-Dimethylaminoethoxy)iminoethyl]-5β-14,15-seco-3β-hydroxy-androstan-14-one;
Z-17α-2-[(2-Aminoethoxy)iminoethyl]-5β-14,15-seco-3β,14β-dihydroxy-androstane;
Z-17α-2-[(2-Dimethylaminoethoxy)iminoethyl]-5β-14,15-seco-3β,14β-dihydroxy-androstane;
Z-17α-(2-Guanidinoiminoethyl)-5β-14,15-seco-3β-hydroxy-androstan-14-one;
Z-17β-Propyl-15-[(2-aminoethoxy)imino]-5β-14,15-seco-3β-hydroxy-androstan-14-one;
Z-17β-Propyl-15-[(2-Dimethylaminoethoxy)imino]-5β-14,15-seco-3β-hydroxy-androstan-14-one;
E,Z-17α-4-[(2-Dimethylaminoethoxyimino)-2-butenyl]-5β-14,15-seco-3β-hydroxy-androstan-14-one;
Z-17α-2-[(2-Aminoethoxy)iminoethyl]-14,15-seco-3β-hydroxy-androstan-14-one;
Z-17α-2-[(2-Dimethylaminoethoxy)iminoethyl]-14,15-seco-3β-hydroxy-androstan-14-one;
Z-17α-(2-Guanidinoiminoethyl)-14,15-seco-3β-hydroxy-androstan-14-one.

* * * * *

UNITED STATES PATENT AND TRADEMARK OFFICE
CERTIFICATE OF CORRECTION

PATENT NO. : 5,955,632

DATED : September 21, 1999

INVENTOR(S) : Mauro GOBBINI, et al.

It is certified that error appears in the above-identified patent and that said Letters Patent is hereby corrected as shown below:

On the title page, item [30] should be:

--[30]  Foreign Application Priority Data
  Aug. 19, 1996  [DE]  Germany  ............ 196 33 376--

Signed and Sealed this

Fifteenth Day of August, 2000

Attest:

Q. TODD DICKINSON

*Attesting Officer*     *Director of Patents and Trademarks*